United States Patent [19]

Guibert

[11] Patent Number: 4,595,008
[45] Date of Patent: * Jun. 17, 1986

[54] LOCALIZED THERMOTHERAPY TECHNIQUE

[75] Inventor: Raul Guibert, Los Angeles, Calif.

[73] Assignee: Sunset Ltd., Los Angeles, Calif.

[ * ] Notice: The portion of the term of this patent subsequent to Aug. 16, 2000 has been disclaimed.

[21] Appl. No.: 521,262

[22] Filed: Aug. 8, 1983

Related U.S. Application Data

[63] Continuation-in-part of Ser. No. 313,313, Oct. 20, 1981, Pat. No. 4,461,299, which is a continuation-in-part of Ser. No. 274,504, Jun. 16, 1981, Pat. No. 4,398,535.

[51] Int. Cl.⁴ ............................................. A61F 7/00
[52] U.S. Cl. .................................................. 128/399
[58] Field of Search ...................... 128/254, 256, 399; 219/528, 527, 211

[56] References Cited

U.S. PATENT DOCUMENTS 3,602,001  8/1971  Bauer .................................. 128/399
3,894,213  7/1975  Agarwala ........................... 128/400

Primary Examiner—Robert Peshock
Attorney, Agent, or Firm—Michael Ebert

[57] ABSTRACT

A localized thermotherapy technique in which heated air is so projected onto a limited surface area on the body of a patient overlying a problem region as to bring about the rapid transfer of heat energy toward this region to raise the temperature thereof without, however, causing undue discomfort or injury to the patient. In apparatus for practicing this technique, air heated to a temperature well above normal body temperature is projected as a high velocity wind toward the limited surface area in a pulsatory thermal-wave pattern, thereby subjecting the area to high-temperature, high-velocity air pulses separated by lower air temperature, relatively static intervals. As a consequence, rapid heat transfer takes place through the body tissue during these intervals, this inward transfer acting to reduce the temperature at the surface to a degree preventing an undue rise thereof. The surface area is protectively coated with a suitable jelly to prevent wind burn and to minimize the outward transfer of heat energy from the surface area to the atmosphere.

15 Claims, 14 Drawing Figures

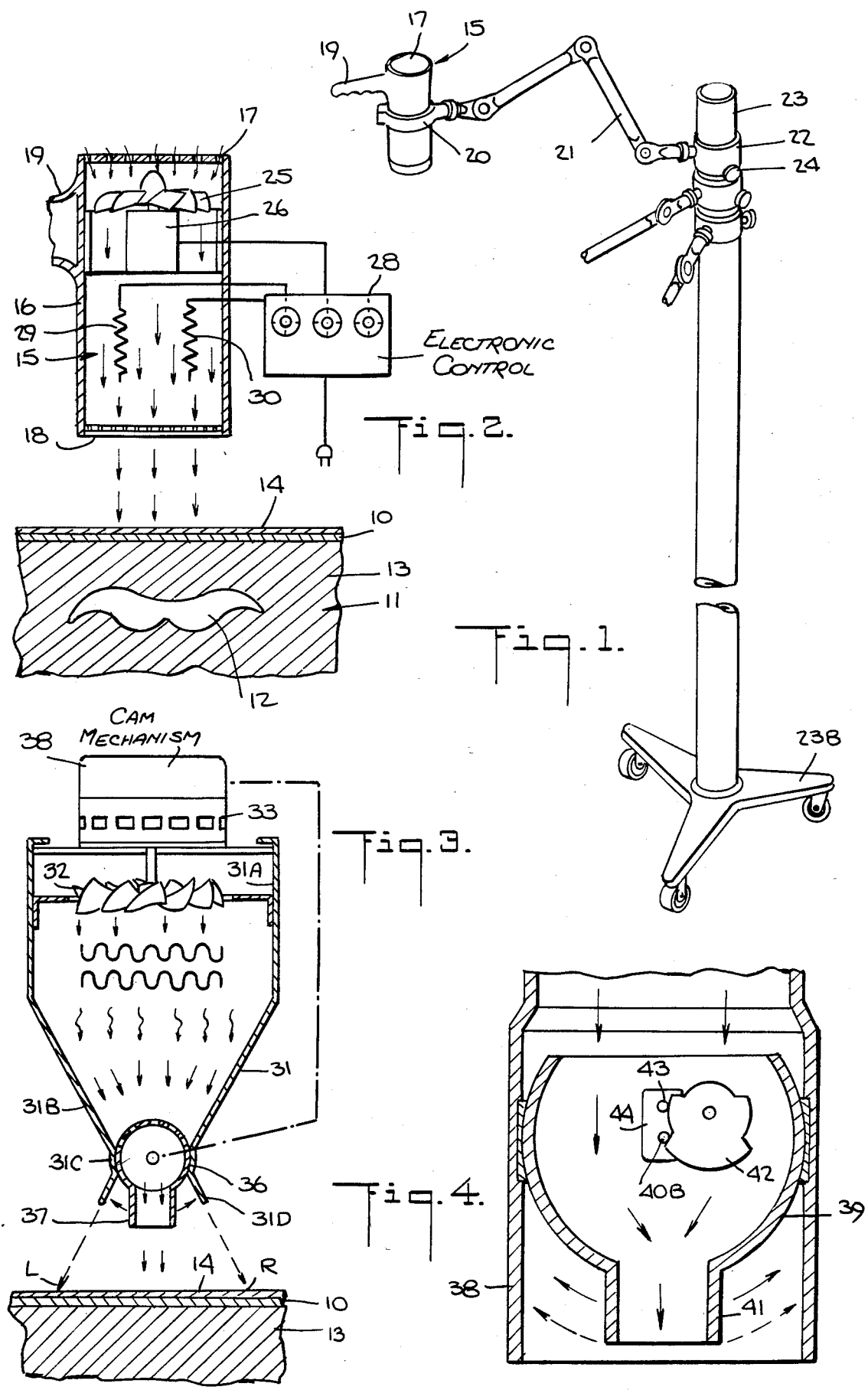

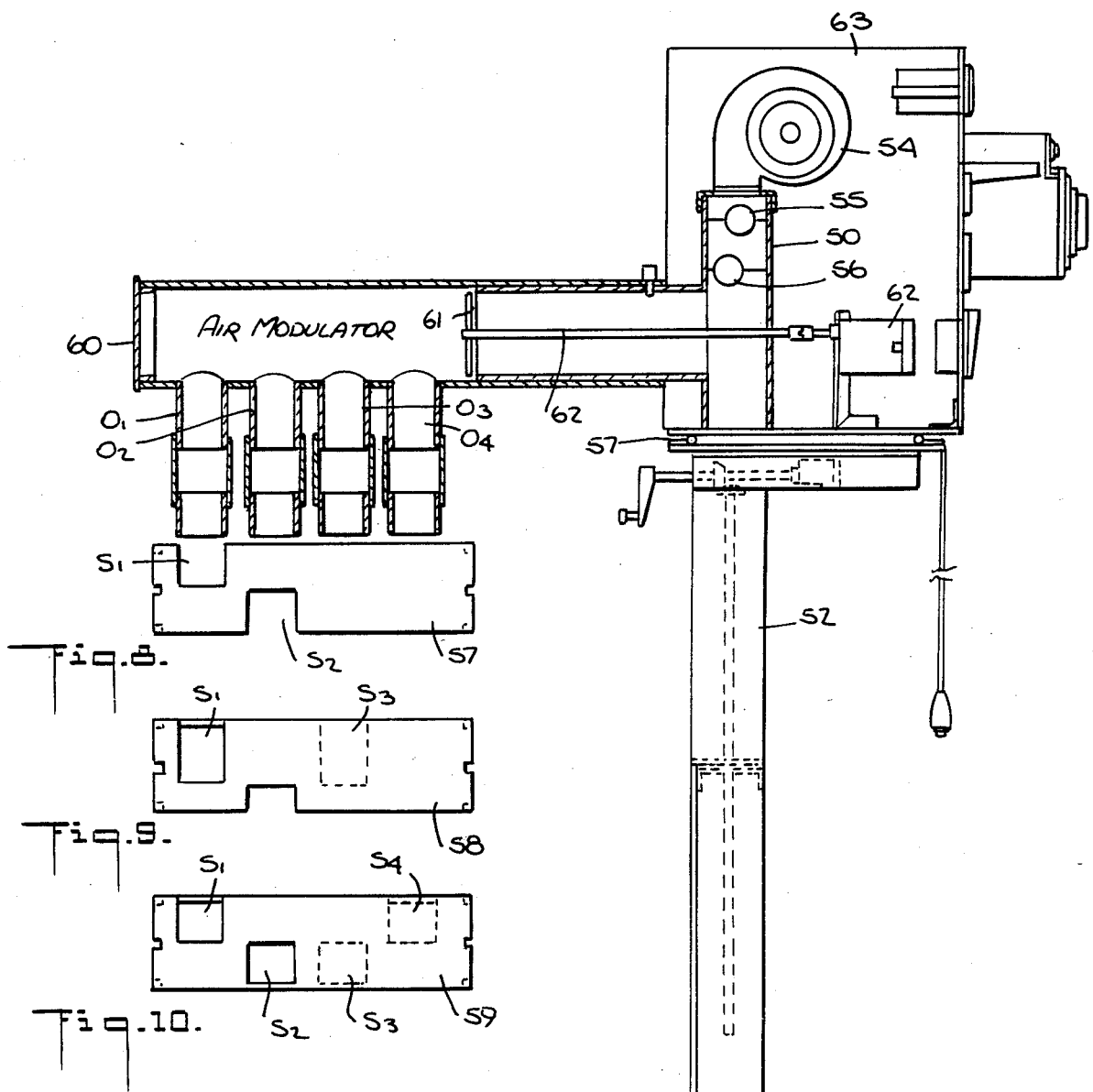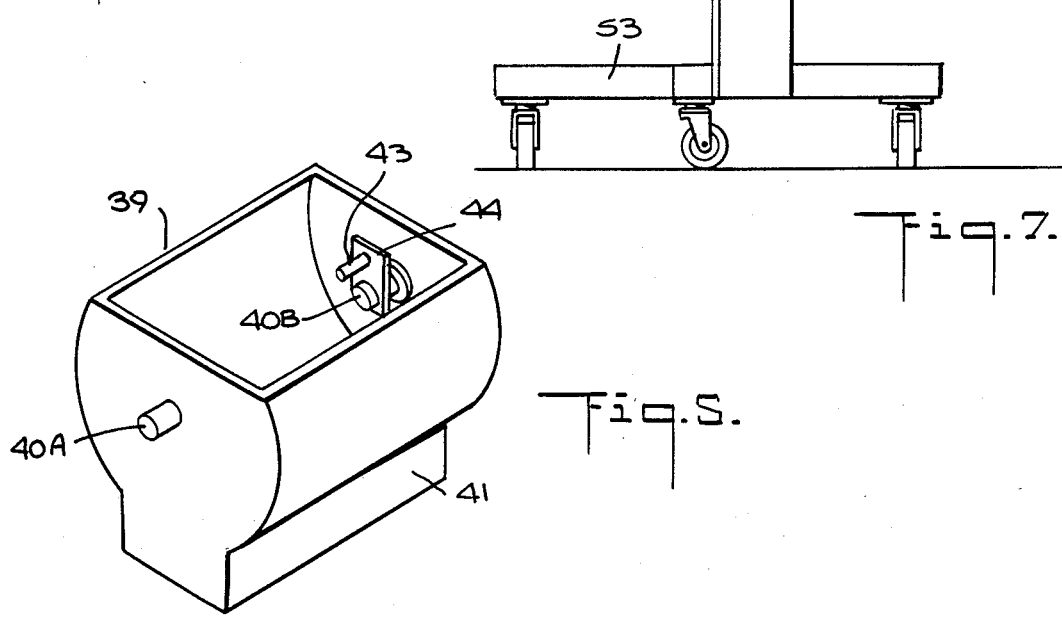

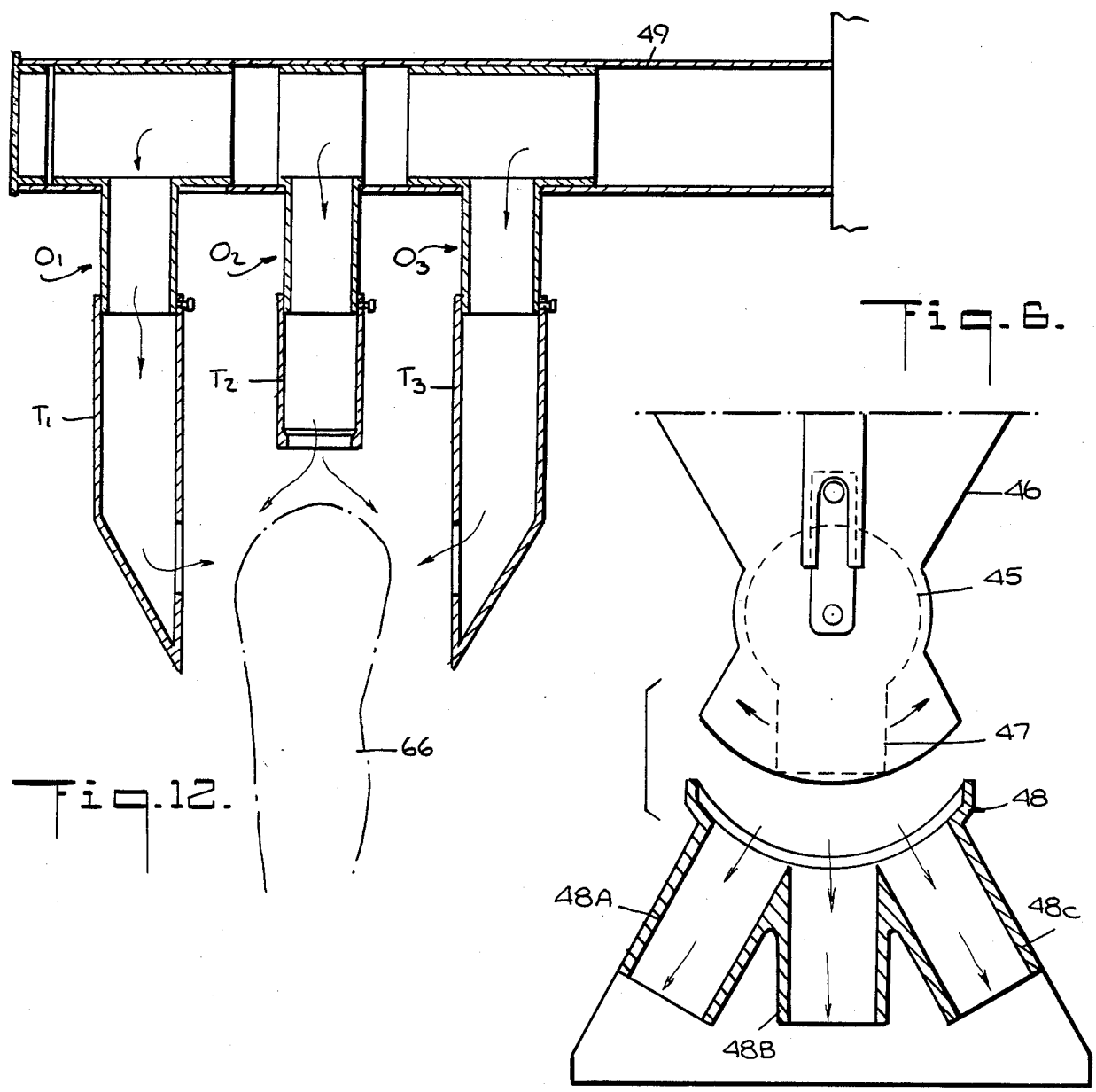
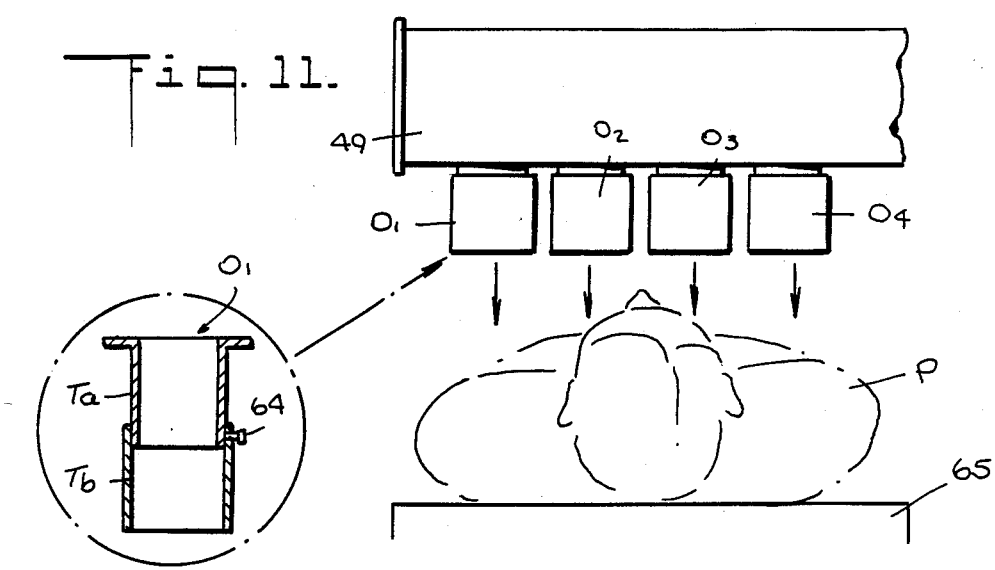

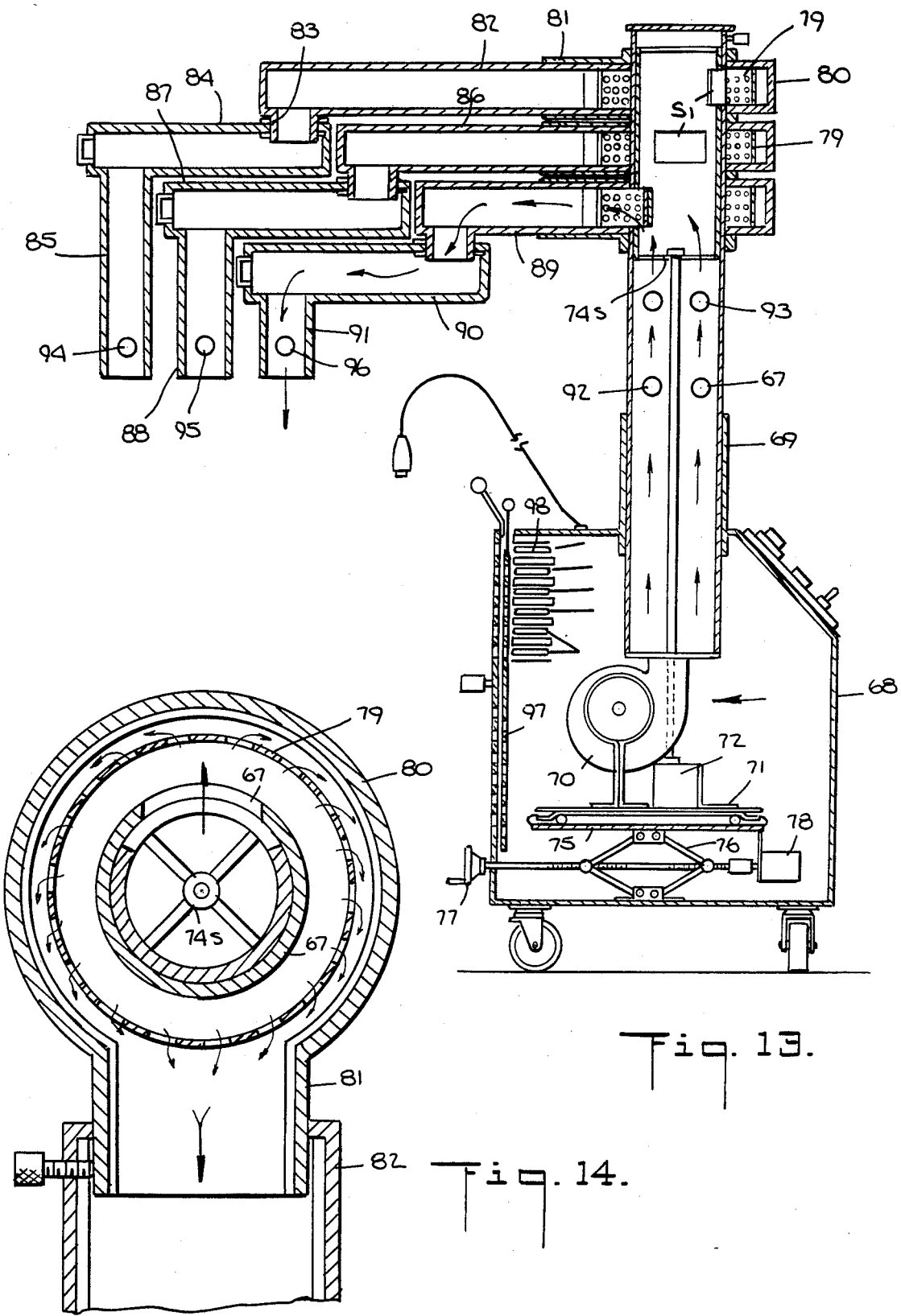

LOCALIZED THERMOTHERAPY TECHNIQUE

RELATED APPLICATIONS

This application is a continuation-in-part of my co-pending Ser. No. 313,313, filed Oct. 20, 1981 now U.S. Pat. No. 4,461,299 issued 7/24/84, which in turn is a continuation-in-part of my still earlier application Ser. No. 274,504, filed June 16, 1981 now U.S. Pat. No. 4,398,535 issued 8/16/81.

BACKGROUND OF INVENTION

Field of Invention

This invention relates generally to thermotherapy, and in particular to a localized thermotherapy technique and an apparatus based thereon in which heated air is projected as a high velocity wind toward a limited surface area on the body of a patient in a pulsatory wave pattern causing rapid inward heat transfer to take place toward an internal problem region underlying this area in a manner raising the temperature of the region without, however, causing undue discomfort or injury to the patient.

The term "problem region" as used herein refers to a tumor, a set of muscles, or any other site underlying the skin which is causing difficulty and which lends itself to treatment by hot or cold therapy.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing.

If the heat produced by a body surpasses heat losses therefrom, this gives rise to fever; but if heat losses exceed heat production, then the body temperature falls below the nominal value, resulting in shivering and hypothermia.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, nor merely to provide warmth, but also to afford a degree of relief or therapy for various conditions. In applying heat to the surface of the body, one may do so by convection, by direct contact with a warmed substance; that is, by conduction, or by radiating energy into the body.

Difficulty has heretofore been experienced in effectively applying heat which is electrically or otherwise generated to a patient. When transferring heat inwardly through living tissue to a problem region underlying the skin, if the heat applied to the skin surface is within a tolerable temperature range, then not enough heat energy is transferred to this site to afford beneficial effects. When, however, the temperature of the applied heat at the skin area is such as to bring about an adequate heat transfer to the problem region, then the skin temperature is usually well above an acceptable level, and this may result in extreme discomfort to the patient and even to the burning of surface tissue.

As pointed out in chapter 10, "Therapeutic Heat" in the text, *Therapeutic Heat and Cold* by Justus F. Lehmann, published in 1982, it is generally accepted that heat produces desirable therapeutic effect, for it increases the extensibility of collagen tissues, it decreases joint stiffness, and it affords pain relief. Moreover, heat relieves muscular spasms, it aids in the resolution of inflammatory infiltrates, edema and exudates, and it enhances blood flow.

It is also now recognized that by heating tumors to a higher temperature than the surrounding tissue, the tumor may be caused to shrink and disappear. As noted in *The New York Times* of April 14, 1982 (section C2) in an article on modern approaches to cancer treatment, the effectiveness of heat therapy is based on the fact that cancers have poor circulation and a reduced ability to dissipate heat. "Thus a temperature of more than 113 degrees Fahrenheit could destroy cancer cells while sparing normal tissue." The concern of the present invention is not with the heat treatment of any particular medical condition or problem region, but with a more effective technique therefor.

While the present invention will be described mainly in connection with thermotherapy or hyperthermia, it is to be understood that a technique and apparatus in accordance with the invention is also applicable to hypothermia treatment in which therapeutic effects are gained by cooling an internal problem region.

SUMMARY OF INVENTION

In view of the foregoing, the main object of this invention is to provide a technique and apparatus based thereon which makes possible localized thermotherapy using exceptionally high temperatures without, however, inflicting injury or causing discomfort to the patient.

More particularly, an object of this invention is to provide a thermotherapy technique which applies a high velocity stream of heated air to a localized skin area overlying a problem region to effect inward heat transfer toward this region to cause the temperature thereof to rise to a level appropriate to the desired treatment without producing an undue rise in the temperature of the surface tissue exposed to the heat that may be damaging thereto.

Also an object of the invention is to provide various species of thermotherapy instruments in varying degrees of complexity which operate in accordance with the technique and are adapted to project a high-velocity, hot air stream toward the localized surface area in a predetermined pulsatory thermal wave pattern.

Still another object of the invention is to provide efficient and reliable thermotherapy instruments which are usable in medical offices, hospitals and in the home, and which may be manufactured and sold at relatively low cost.

Briefly stated, in a technique in accordance with the invention and in thermotherapy apparatus based thereon, air heated to a temperature well above normal body temperature is projected as a high velocity stream in a pulsatory wave pattern toward a localized skin area overlying a problem region, thereby subjecting this area to high-velocity heated air pulses separated by lower air temperature, relatively static intervals.

The pulsatory wave pattern is created by apparatus which operates in a periodic interruption mode, in a cyclical stepping mode or in a cyclical sweeping mode, depending on the nature of the instrument and its intended applications.

As a consequence of the pulsatory wave pattern, heat transfer takes places through the body tissue toward the problem region during the intervals between the pulses, this inward transfer acting to reduce the temperature at the skin surface to a degree preventing an undue rise thereof. While during the pulse periods the temperature of the hot air at the skin surface is much higher than body temperature, the duration of each pulse is relatively short and insufficient to cause discomfort or injury to the patient.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a first preferred embodiment of a thermotherapy instrument in accordance with the invention;

FIG. 2 is a sectional view of the heat applicator included in this instrument;

FIG. 3 is a sectional view of the heat applicator included in a second preferred embodiment;

FIG. 4 is a sectional view of the heat applicator included in a third preferred embodiment;

FIG. 5 is a perspective view of the heat applicator shown in FIG. 4;

FIG. 6 shows, in section, a heat applicator for use in a fourth preferred embodiment of the invention;

FIG. 7 is an elevational view of a fifth preferred embodiment of an instrument in accordance with the invention;

FIG. 8 illustrates one form of a tubular air modulator to be used in the first embodiment:

FIG. 9 illustrates a second form of air modulator;

FIG. 10 illustrates a third form of air modulator.

FIG. 11 shows a patient lying under the outlets of the instrument shown in FIG. 7 for treatment of his chest area;

FIG. 12 shows the knee of a patient with the instrument of the type in FIG. 12 arranged to apply heat thereto;

FIG. 13 illustrates, in section, a sixth embodiment of a thermotherapy instrument; and FIG. 14 is a transverse section taken through FIG. 13.

DESCRIPTION OF INVENTION

The Basic Technique:

In order to generally demonstrate the value of thermotherapy in the treatment of problem regions, we shall consider one of the most common of all human afflictions; namely, the backache. As noted in the "Book of Back Care," published by the American Medical Association, at some time in our lives most of us suffer from backache.

The back is an extraordinarily complex structure. It is composed of bones, cartilage, nerves, blood vessels and layers upon layers of muscle, each with its own potential for causing trouble. In physical therapy, heat is most often used to help relax tense and spastic back muscles. As indicated in the "Book of Back Care," heat is usually applied to the skin overlying the problem region with hot towels, hot water bottles, electric heating pads, infrared lamps or paraffin baths.

Because in all conventional heat applicators, the heat is applied continuously to the skin area overlying the problem region, this imposes strict limits on the acceptable temperature level. Thus if one seeks to have the heat penetrate more deeply into the body, the temperature at the surface area must be raised to promote more rapid heat transfer. But a point is then quickly reached at which the patient is made uncomfortable—for one can only tolerate continuously applied heat whose temperature level is only a few degrees above body temperature. Raising the temperature above the tolerance level in order to effect greater body penetration will cause injury to the patient.

Because continual heat therapy techniques, to be completely safe, must operate at a relatively low temperature level, they are of limited effectiveness in the treatment of backache and other painful conditions that are relieved by heat.

In a thermotherapy technique in accordance with the invention, the heat energy applied to a localized skin area overlying a problem region in the body of the patient is in the form of an air stream at an elevated temperature level, such as 130 to 140 degrees F. or higher, well above normal body temperature, such that if the heat and air were to be applied continuously for even a few minutes, though it would act to promote rapid inward heat transfer, it would at the same time cause extreme discomfort and injury to the patient.

In order, therefore to render the applied heat energy tolerable and at the same time bring about a rapid inward heat transfer from the skin area to the problem region, the heat energy in a technique in accordance with the invention is applied in a pulsatory thermal air wave pattern.

The nature of this pulsatory air wave pattern is such that no section or sub-division of the localized skin area is subjected to high temperature heating for more than a brief period; i.e. a period having a one to three second duration, which is insufficient to cause discomfort or burning. This period is followed by a relaxation interval at a lower air temperature not much higher than body temperature. In practice, the relaxation interval may have a duration of about one to four seconds. Typically in a heat applicator in accordance with the invention, the wave pattern is produced by periodic pulses having a one second duration followed by one second intervals.

The factors which come into play in determining an acceptable pulsatory wave pattern are the air temperature, the flow velocity, the duration of the pulse and the duration of the interval. Obviously, with higher temperatures or higher air flow velocities, the pulse duration must be shorter.

The pulsatory thermal air wave pattern is created by heat applicators that operate in one of three modes. In one mode, a stream of hot air is blown at high velocity toward the localized skin area to impinge thereon and to flow across the area, this stream being periodically interrupted so that the localized skin area being subjected to treatment is exposed to high temperature heat energy for no more than a brief period insufficient to cause discomfort, followed by a relatively static relaxation interval at a markedly lower air temperature during which rapid heat transfer takes place through the body tissue toward the problem region. This inward transfer acts to reduce the temperature at the surface to a degree preventing an undue rise thereof.

In the second mode, the stream of hot air which is blown at high-velocity toward the skin area does not at any one time engage the entire area but takes the form of a beam which is cyclically shifted in discrete steps from one sub-division or zonal section of this area to the next, to thereby fully transverse the area in the course of each cycle. In this way, each zone is subjected periodically to a high velocity pulse of hot air followed by a relaxation interval.

In the third mode, the high velocity stream of hot air is blown toward the localized skin area and cyclically swept thereacross to effectively expose the entire area to periodic pulses of hot air separated by relaxation intervals.

Regardless of the mode of operation, since no zone of the localized skin area is ever subjected to a high velocity flow of hot air for more than a brief period, this burst of hot air is referred to herein as a pulse. Because heated air flows over the skin area at high velocity, this forced convection results in rapid heat transfer between the hot air passing over the skin surface and the lower temperature tissue thereunder.

During the relaxation intervals between these pulses, the air is relatively static and has a low thermal capacity; but because of residual heat in the region above the localized skin area, the air temperature is a few degrees above skin temperature. This prevents the outward release of heat from the body to the atmosphere. It is important to note at this point that the pulsatory technique is not applicable to liquids, for while one could pulse the flow of liquid, in the relaxation interval the high thermal capacity of liquids would supply an undue amount of heat to the skin.

The high-velocity air stream is effectively a high wind; and in order to prevent windburn, the skin subjected thereto is protectively coated with petroleum jelly or a similar viscous product judicially compatible with the skin. This layer also acts to minimize the outward transfer of heat energy from the skin area to the atmosphere. The heat applicator must be spaced and not in contact with the skin surface because of residual heat in the applicator.

To give an example of how heat transfer takes place, we shall assume that the outer layer of the localized skin area is initially at a normal body temperature of 98.6° F. We shall further assume that each high temperature air pulse is at 140° F. and that the pulse lasts one second, the flow velocity across the skin, at about 1700 feet per minute. Thus the first pulse flows past the skin area at high velocity to raise the temperature of the outer layer from 98.6° F. to, say 101° F.

Then during the relatively static air interval which follows during which we will assume that the ambient air temperature is, say, 102° F., heat from the outer layer will transfer inwardly toward a second and inner layer, which is thereby raised in temperature to, say, 99° F., with a resultant reduction in the temperature of the outer layer to, say, 100° F.

Thus the interval between the hot air pulses represents a relaxation period during which heat transfer takes place from the outside in, but not from the inside out; for the temperature outside the skin is always above the body temperature. When the outer layer, now at 100° F., is again subjected to the next hot air high-velocity pulse at 140° F., this will raise the temperature of the outer layer another notch, and the temperature of this layer will again be somewhat reduced during the following interval when heat is transferred from the outer layer to the next layer.

It is important to bear in mind that because of the high pulse velocity, a large volume of air is brought into heat exchange relationship with the skin during the pulse period, whereas in the interval, it is only a small volume of relatively static air that exists between the skin and the heat applicator.

Similar heat transfer actions take place concurrently between the second and third layers underlying the skin layer and between the third and fourth layers, and so on, toward the problem region, very much in the fashion of an electronic cascade counter in which when an input signal (heat pulse) is received, the state of each stage (layer) in the cascade is advanced in an ordered sequence.

A technique in accordance with the invention makes it possible to produce a much greater rise in the temperature of an internal problem region underlying a limited skin area subjected to the heat without, however, discomfort to the patient or damage to the tissue being heated. Because the internal heat is significantly higher in temperature than that heretofore obtainable without discomfort or damage, the beneficial effects are far more pronounced.

While it has been known since ancient times that by inducing, as it were, a localized fever in a problem region, one can reduce pain and obtain thereapeutic effects, the mechanism by which the heat acts is not fully understood. The theory underlying a technique in accordance with the invention, as presently understood, is based on the reaction of the nervous system to thermal stimuli that is interpreted by the system as representing fever or an abnormal temperature, even though no fever is physiologically produced. As distinguished from conventional techniques, the present technique makes use of temperatures which, if applied continuously, would simulate a localized body fever.

The nervous system is composed of an extensive network and special tissue that controls and correlates the actions and reactions of the body and its adjustment to the environment. The network consists of a brain and spinal cord which together constitute the central nervous system operating in conjunction with a system of the peripheral nerves which carries nerve impulses or signals to and from the central nervous system. The afferent or sensory fibers convey impulses arising from stimulation of the end organs, as by touch or heat, to muscles and other parts of the body that respond to stimulation.

In many areas of the body, the fibers of a sensory nerve cell and those of a motor nerve cell are interlacing, forming a minor nerve center or reflex arc. Thus, when a finger touches a heated object, the finger is withdrawn instantaneously, for the sensory impulse has stimulated the motor impulse in a reflex arc long before the sensing impulse reaches the brain.

It is well known that the nervous system is capable of carrying out emergency procedures. Thus when an injury occurs to a particular part of the body, the nervous reaction is a swelling of blood cells near the site clearing the way for emergency measures which include tiny pharocyte cells that pour into the area to consume dirt, bacteria, viruses, and dead and injured cells. When however the injury is not localized, the capacity of the body is insufficient to provide a reaction capable of coping with a widespread condition.

Because the nervous system acts in response to stimuli to relieve pain, it is now known to use electrical stimulation for this purpose. Thus in the paper entitled "New Methods for Achieving Pain Control by Transcutaneous Nerve Stimulation" presented to the American Academy of Neurology, Toronto, April 1976, by Richard L. Stieg, it is pointed out that while the physiological basis for the success of such stimulation is poorly understood, the fact remains that the technique holds great clinical promise.

Nerve stimulation by heat at a level well above normal body temperature in a technique in accordance with the invention is believed to produce a physiological reaction resulting in the swelling of blood vessels, as in an actual localized trauma, and in bringing to the site an enhanced supply of blood and a multitude of cells which function to relieve or remedy the condition at the problem region that resulted in pain.

The present invention differs significantly from prior thermotherapy techniques in that it makes it possible to stimulate the nervous system with much higher temperatures than has heretofore been feasible to bring about a beneficial reaction without, however, causing discomfort to the patient or injury to the surface of the local site being treated.

A publication pertinent to the present technique is the article, "Enhancement of Diffusive Transfer by Periodic Pulsation" by Putterman and Guibert, in Applied Scientific Research (1983).

First Embodiment:

Referring now to FIGS. 1 and 2, shown therein is a thermotherapy instrument in accordance with the invention which operates in the first mode; that is, by periodically interrupting a high-velocity hot air stream directed toward a localized skin area 10 on the body of a patient 11. This area overlies a problem region 12, such as tensed muscles, a mass of tissue 13 lying in the path between skin surface 10 and the problem region.

In order to explain how heat is transferred from the skin surface to the problem region, we shall assume that the tissue mass 13 is composed of a skin layer and a series of inner layers, the innermost abutting problem region 12.

Skin surface 10 is coated with a protective outer layer 14 of petroleum jelly or a similar protective grease that is sterile and non-reactive with the skin. This outer layer serves not only to prevent wind burn but also to resist the outward transfer of the heat from the body of the patient to the atmosphere. The boundaries of the skin area on which the hot air stream impinges are not critical, for the nature of the technique is such that excessive skin heating is never encountered. It is, of course, desirable to concentrate the stream onto the localized skin area.

A high-velocity stream of air heated to a temperature well above normal body temperature is directed toward skin area 10 by a heat applicator, generally designated by reference numeral 15. The applicator includes a cylindrical casing 16 whose opposing input and output ends 17 and 18 are provided with screens to admit ambient air at the inlet and to discharge heated air at the outlet.

Heat applicator 15 is provided with a handle 19 and is attached by a clamp 20 to an articulated arm 21 extending from a coupling ring 22. Ring 22 is slidable along a vertical pole 23 to assume an elevation thereon which is fixed by a set screw 24. The pole is anchored on a three-arm wheeler base 23B. More than one such ring and associated articulated arms are fitted on the pole so that the same pole can serve to support several applicators. Because these coupling rings are each rotatable on the pole, their angular positions may be changed and set so that one applicator is, say, to the left of the pole, another is to the right, and so on. The instrument is on wheels and it may therefore be moved to any desired site to treat more than one patient at a time.

Applicator 15 is provided with a suction fan 25 adjacent input end 17, the fan being driven by a motor 26. The motor operation is governed by an electronic control center 28 which also acts to regulate the operation of low and high temperature electrical heating elements 29 and 30.

Applicator 15 is provided with a suction fan 25 adjacent input end 17, the fan being driven by a motor 26. The motor operation is governed by an electronic control center 28 which also acts to regulate the operation of low and high temperature electrical heating elements 29 and 30.

In operation, ambient air drawn into the casing by the fan is propelled at high velocity toward the outlet of the applicator to be projected as an air stream in the direction of the localized skin area. The air in the applicator is heated by heater elements to an elevated temperature level well above body temperature.

The electronic control center is energized from a commercial power line and is provided with an electronic motor pulsor whose duty cycle is manually adjustable by control knobs so that the motor is caused to turn "on" and "off" periodically for an "on" period of, say, 2 seconds and a somewhat longer "off" interval of, say, 3 seconds, depending on the desired form of the pulsatory wave pattern. The speed of fan rotation and the operating temperatures of the heaters are adjustable from the control center. Thus by operating both heaters 29 and 30 simultaneously, one attains the maximum temperature level. All variables to obtain a desired pulsating thermal wave pattern are settable from the center.

Also included in the control center is an adjustable timer to shut off the applicator after a preset period. The patient may be provided with a safety switch connected to the power line cable to cut off the applicator should he feel discomfort as a result of excessive heat.

The position of the heat applicator relative to the localized skin area and the distance between the outlet of the applicator and this area are readily adjustable in the instrument shown. Thus if the skin area to be treated is relatively broad, the applicator is then sufficiently spaced from this area so that the air stream impinges over the entire area.

In place of articulated arm 21, one may use pantograph arms of the type commonly used on desk lamps. Also, rather than pulse the applicator by periodically interrupting the operation of the fan, this fan may be operated continuously and a rotating shutter provided at the outlet to periodically interrupt the air discharged therefrom.

Second Embodiment:

The heat applicator shown in FIG. 3 may be mounted on an articulated arm extending from a pole in the same manner shown in FIG. 1. In this applicator, which operates in the cyclical sweeping mode, the casing 31 has a rear cylindrical section 31A which houses a suction fan 32 driven by an external motor 33, electrical heaters 34 and 35 being disposed within the casing in advance of the fan.

The ambient air drawn into the casing from the rear inlet is heated and propelled through a conical intermediate section 31B of the casing to penetrate the perforations of an oscillating scanning drum 36. This is mounted for rocking motion in a conforming throat section 31C of the casing that leads into a divergent outlet section 31D.

Scanning drum 36 is provided with a projecting outlet port 37 which, as the drum rocks, sweeps back and forth within a sector defined by the side walls of outlet section 31D, as shown by the arrows in FIG. 3. Rocking of the drum is effected by a suitable cam mechanism 38 coupled to the shaft of motor 33 and operatively linked to the center shaft of drum 36.

Thus the high-velocity beam of heated air projected from oscillating port 37 of the applicator is caused cyclically to sweep back and forth to traverse the localized skin area 10 of the patient. The beam cross section is determined by that of port 37 which is preferably rectangular. But the invention is not limited to a beam of this shape.

As a consequence, the beam, in the course of an operating cycle, first impinges on that zone or sub-section of the skin area adjacent the left side of the air radiation sector, as indicated by arrow L, and then proceeds across the skin area until it reaches the zone of the skin area adjacent the right end of the sector, as indicated by arrow R, at which point the sweep direction is reversed.

Thus, if one regards the skin path extending between the left and right sides of the radiation sector as composed of a series of skin zones, no one zone is continuously exposed to the high velocity beam. The brief exposure period for each skin zone is determined by the scanning speed and is followed by a relaxation interval.

Hence each skin zone or sub-section is subjected to a pulsatory thermal wave pattern. The inner heat transfer taking place during the intervals between pulses draws heat away from the skin surface and acts to progressively raise the temperature of the problem region.

In this instance, the area of skin traversed by the scanning beam is determined by the distance between the heat applicator and the skin, the shorter this distance, the narrower the angular sector between point L & R on the skin surface.

In practice, the motor for fan 32 need not be mounted on the casing but may be coupled to the casing fan from a remote position by a flexible cable. Or the fan may be omitted from the applicator casing and air from a remote blower may then be blown into the applicator casing through a flexible tube.

Third Embodiment:

The heat applicator shown in FIGS. 4 and 5 is similar to that shown in FIG. 3 and also includes a scanning mechanism to produce a beam which sweeps cyclically across the localized skin area, causing the applicator to operate in the cyclical sweeping mode.

In this instance, disposed in the outlet section of a casing 38 through which heated air is blown is a trough-shaped scanner 39 which is pivotally mounted on trunnions 40A and 40B within casing 39. The scanner is provided with an outlet port 41 having a rectangular cross section to project a high velocity beam having the same cross section.

The scanner is caused to rock back and forth and thereby sweep within an angular sector limited by the opposing walls of casing 38. This is effected by means of a contoured cam 42 whose shaft 43 is driven by a motor mounted on the exterior of the casing.

Cam 42 engages a pin 43 on a rocker plate 44 secured to trunnion 40B, so that in the course of each revolution of the cam, the scanner is caused to rock back and forth and the beam projected therefrom is caused to sweep across the limited skin area from one end to the other and back, as in the case of FIG. 3.

In the applicator arrangements shown in FIGS. 3 and 5, all of the heated air produced thereby is blown toward the patient, and from there it escapes to the room or office occupied by the patient. In prolonged operation, this action may raise the room temperature to an uncomfortable level should the room not be adequately ventilated or air conditioned. In practice, therefore, use may be made in the applicator of cross-flow blowers in conjunction with casings so designed as to recirculate a portion of the hot air and thereby reduce the volume of hot air discharged into the room.

In the applicators shown in FIGS. 3, 4 and 5, the fan is always on and a cyclical sweeping operating mode is produced by a scanning action, not by an interruption or shutter action.

Fourth Embodiment:

The applicator shown in FIG. 6 is similar to that in FIG. 3 in that it includes a scanning drum 45 operating within the throat section of a casing 46, the drum having an outlet port 47 which projects a hot air beam at high velocity, the drum rocking back and forth.

However, in this instance, the beam projected from port 47 is forced to flow sequentially through a set of three outlets 48A, 48B and 48C of an accessory 48 mounted over the outlet section of the casing. These outlets are progressively angled so that their respective axes radiate from a common point.

As a consequence, the beam emitted by port 47 passes successively through outlets 48A, 48B and 48C to impinge on the skin area to be treated, and to step sequentially from one zone or sub-section of the skin area to the next to traverse the entire area from one end to the other, and then to reverse the stepping action. This applicator therefore operates in the cyclical stepping mode rather than in the cyclical sweeping mode, so that each zone of the skin area is given a discrete heat treatment.

Fifth Embodiment:

In the applicator shown in FIGS. 7 to 10, a cylinder 49 is cantilevered from a hollow vertical column 50. This column is mounted on a turntable 51 which is supported on a telescoping post 52 mounted on a wheeled base 53 in an arrangement making it possible to elevate column 50 to a desired height and to rotate the column and thereby cause horizontally-extending cylinder 49 to assume a desired orientation with respect to a patient.

Air is blown into column 50 by means of a blower 54 mounted on top of the column, the air being heated by electrical heaters 55 and 56. The resultant high-velocity hot air stream is forced into cylinder 49 within which is a replaceable tubular air modulator, such as a modulator 57, 58 or 59, shown separately in FIGS. 8, 9 and 10.

The modulator is installed in cylinder 49 through an end opening normally closed by a removable cap 60. One end of the modulator is coupled to drive disc 61 rotated by a shaft 62 passing coaxially through cylinder 49 and driven by a motor 62 disposed within a housing 63 mounted on turntable 51.

Extending laterally from the underside of cylinder 49 is a row of four outlets $O_1$ to $O_4$. The tubular air modulator which rotates within cylinder 49 is provided with arcuate slots which cooperate with the cylinder outlets and are circumferentially displaced so that at any one time in the course of a full revolution, only one slot is in registration with its complementary outlet $O_1$ to $O_4$.

In the air modulator 57 shown in FIG. 8, there is an arcuate slot $S_1$ on the circumference of the tube which, in the course of each revolution, is aligned with output port $O_1$ to permit the high-velocity hot air to be discharged from the modulator through this output port for a period determined by the arcuate length of the slot relative to that of the circumference, as well as the rate of rotation.

There is also an arcuate slot $S_2$ of the same dimensions as slot $S_1$, but diametrically opposed thereto on the circumference of the tube. When slot $S_2$ is aligned with output port $O_2$, it permits the hot air to shoot out of this port at high velocity. No slots are provided with respect to ports $O_3$ and $O_4$ which are always blocked. Hence when modulator 57 is installed in cylinder 49, only ports $O_1$ and $O_2$ are operative to provide alternate pulses of hot air at high velocity in the course of each cycle.

Since these pulses are projected as beams from spatially separated ports, the instrument operates in the cyclical stepping mode, one beam impinging on one zone of the skin area and the other on the adjacent zone, the two zones together defining the localized skin area being treated. This modulator is appropriate for relatively small skin areas to be heated by the instrument.

The air modulator 58 (FIG. 9) has three arcuate slots $S_1$, $S_2$ and $S_3$ at angularly displaced circumferential positions (120° apart) which, in the course of a full revolution, are sequentially aligned with the respective output ports $O_1$, $O_2$ and $O_3$. The port $O_4$ is always blocked. Hence when this modulator is installed in cylinder 49, beams of high-velocity hot air are sequentially projected from ports $O_1$, $O_2$ and $O_3$.

The air modulator 59 (FIG. 10) has four arcuate slots $S_1$, $S_2$, $S_3$ and $S_4$ at angularly displaced circumferential positions (90° apart), so that in the course of a full revolution, the slots are sequentially aligned with the respective output ports $O_1$ to $O_4$, no port being blocked.

Each telescoping port, as shown in FIG. 11 in connection with port $O_1$, is constituted by telescoping tubular sections $T_a$ and $T_b$, the section $T_b$ being more or less extended on section $T_a$ to adjust the effective length of the port, as required. A set screw 64 is provided to hold the adjusted length.

Thus when a patient P, as shown in FIG. 11, lies on a table 65 under the ports of the instrument with his chest exposed thereto, use may be made of air modulator 59 to cause sequential stepping of the high-velocity beam across the chest to effect treatment of a problem region in the chest area. However, if the skin area to be exposed to heat is rounded or contoured, the length of the ports may be readily adjusted to conform the projected beams to the contour of the skin area to be heated, so that each port is spaced the same distance from the skin as all others.

In FIG. 12, which shows a knee 66 being treated in an instrument having only three ports $O_1$, $O_2$ and $O_3$, these are provided with telescoping extensions $T_1$, $T_2$ and $T_3$. Extensions $T_1$ and $T_3$ have lateral openings to project their beams onto opposing sides of the knee. The mid port $O_2$ projects its beam toward the top of the knee, so that the knee is uniformly treated.

In this instrument, one is able to adjust the height of the cylinder 49 and its angular position in azimuth so that it is properly oriented with respect to the skin area of the patient to be treated.

Sixth Embodiment:

Referring now to FIGS. 13 and 14, there is shown an instrument capable of producing sequential beams of high-velocity hot or cold air, depending on whether the patient is in need of hyperthermia or hypothermia treatment. Thus, in the case of patients who are athletes, treatment in some instances involves first the application of cold, as by a compress, and then heat. With the present applicator, the same instrument carries out either function.

The instrument includes a hollow, vertical column 67 axially slidable within a sleeve 69 protruding above the upper wall of a wheeled housing 68 so that the column may be shifted to extend further into the housing or elevated relative to the housing.

An air blower 70 coupled to the lower end of column 67 is supported by a bracket on a turntable 71 on which there is also mounted a motor 72 for rotating a vertical shaft 73. This shaft extends coaxially through columns 67 and drives a spider 74S at the lower end of a tubular air modulator 74 which is rotatable within the upper end of the column. This modulator 74 is of the type shown in FIGS. 8 to 10 and includes three angularly-displaced arcuate slots $S_x$ which are sequentially operative with respect to corresponding openings in the column.

Turntable 71 rests on a platform 75 which may be raised or lowered by a jack 76 operated through a lead screw by a motor, or manually by a crank wheel 77. Thus one may adjust, as required, the elevation of the applicator structure cantilevered from the upper end of column 67.

The applicator structure is constituted by a set of three articulated-arm port assemblies, one above the other, each separately rotatable relative to the column so that the respective assemblies may be caused to assume different angular positions to orient their ports relative to a limited skin area of a patient in a manner conforming thereto.

The upper end of column 67 is provided at progressively higher levels corresponding to the levels of the arms cantilevered therefrom with a set of three lateral openings $67_{op}$ (see FIG. 14). These openings sequentially register with the arcuate slots $S_x$ in the course of each revolution of air modulator 74 in a manner similar to the arrangement in FIG. 7.

Concentric with each opening $67_{op}$ is an annular shield 9 which serves to equalize the pressure of air blown out of the lateral opening. The pressurized air penetrating the perforations of the shield is received in a doughnut-shaped collector 80 surrounding the shield and provided with a lateral nozzle 81. Each collector is separately rotatable on the column.

The uppermost articulated arm is composed of a hollow main section 82 coupled at one end to nozzle 81 which is at said level, the other end being pivotally connected by an underside coupler 83 to a hollow minor section 84 provided at its underside with a downwardly projecting outlet port 85. Thus one is able to swing main section 82 relative to the column and to swing the minor section relative to the main section to adjust the port position.

The intermediate articulated arm has a hollow main section 86 coupled to nozzle 81 at the same level, the other end of main section 86 being pivotally linked to a hollow minor section 87 provided with a port 88 which depends therefrom. Similarly, the lower articulated arm is composed of a main section 89, a minor section 90 and a port 91 depending therefrom.

The relative lengths of the various sections of the three articulated arms are such that when all arms occupy the same vertical plane, the lower arm nests within the intermediate arm which nests within the upper arm, the outlets of the ports all being at the same height. When, however, the arms are swung out, they may be caused to assume whatever geometric pattern is appropriate to the skin area of the patient to be treated.

For therapeutic heating, electrical heating elements 92 and 93 are then energized, these elements being disposed within column 67 to heat the air blown therethrough, so that hot air is projected at high velocity sequentially from ports 85, 88 and 91 to impinge on the skin area of a patient. The instrument functions in the cyclical stepping mode in the manner previously described. Additional heat may be supplied by also energizing electrical heating elements 94, 95 and 96 disposed in ports 85, 88 and 91, respectively.

For therapeutic cooling, ambient air drawn through housing 68 by the blower 70 passes through an adjustable louver 97 in one side wall of the housing, the air then flowing through a stack of gel pads 98 that have been previously refrigerated so that the pads remain for a prolonged period at a temperature well below 32° F., the freezing point of the gel being much lower then that of water. Alternatively, the incoming air may be reduced in temperature by suitable thermo-electric junction elements of the type used in non-mechanical refrigeration units.

Thus when operating to effect hypothermia treatment, the electrical heating elements are inactive and the air blown through the column is at a reduced temperature appropriate to the nature of the therapy, the unit operating in the cyclical stepping mode.

The other embodiments may also be adapted to provide cold air therapy. Thus in the applicator shown in FIG. 2, one can couple the inlet end of the casing by a flexible hose to a compact refrigerator to produce a high-velocity beam of chilled air which is periodically interrupted by a rotating shutter disposed at the outlet, the motor used to drive the suction fan also turning the shutter.

While there have been shown and described preferred embodiments of a localized thermotherapy technique in accordance with the invention, it will be appreciated that many changes and modifications may be made therein without, however, departing from the essential spirit thereof.

I claim:

1. A localized therapeutic hyperthemia or hypothermia technique for treating a problem region in the body of a patient which underlies a limited skin area without injury to the skin area, the technique comprising the steps of:
   A. generating a high-velocity stream of air having a predetermined temperature level that deviates from the normal body temperature level of the patient so that a marked differential exists therebetween to promote rapid heat transfer; and
   B. directing said stream to flow across said skin in a pulsatory wave pattern in a manner whereby no zone of said skin area is subjected to said stream for more than a relatively brief pulse period during which said zone is exposed to said high-velocity air at said predetermined level, the pulse periods in said wave being separated by intervals during which the air over the skin area is relatively static, the intervals having a duration sufficient to permit rapid heat transfer to then take place between the skin area and the problem region to an extent preventing a deleterious change in the temperature of the skin area.

2. A technique as set forth in claim 1, wherein said predetermined temperature level is higher than said body temperature level to afford heat therapy, and the parameters are such that deleterious overheating of said skin area is prevented.

3. A technique as set forth in claim 1, wherein said pulsatory wave pattern is generated by periodically interrupting the stream flowing past said area to produce said high-velocity pulses separated by said intervals.

4. A technique as set forth in claim 1 wherein said pulsatory wave pattern is generated by cyclically sweeping said stream back and forth across said skin area.

5. A technique as set forth in claim 1, wherein said pulsatory wave pattern is generated by cyclically stepping said stream to traverse in sequence the series of zones which constitute said area.

6. A technique as set forth in claim 1, wherein said skin area is coated with a protective layer of petroleum jelly.

7. An instrument adapted to therapeutically treat a problem region in the body of a patient underlying a limited skin area, said instrument comprising:
   A. means to generate a high-velocity stream of air having a predetermined temperature level that deviates from the normal body temperature level of the patient so that a marked differential exists therebetween to promote rapid heat transfer; and
   B. means to direct said stream to flow across said skin in a pulsatory wave pattern in a manner whereby no zone of said skin area is subjected to said stream for more than a relatively brief pulse period during which said zone is exposed to said high-velocity air at said predetermined level, the pulse periods in said wave being separated by intervals during which the air over the skin area is relatively static, the intervals having a duration sufficient to permit rapid heat transfer to then place between the skin area and the problem region to an extent preventing a deleterious change in the temperature of the skin area.

8. An instrument as set forth in claim 7, wherein the generating means and the directing means are constituted by a heat applicator mounted on a stand, the position of the applicator relative to a patient being adjustable.

9. An instrument as set forth in claim 8, wherein said applicator includes a suction fan disposed in said casing to draw air from one open end thereof and to blow it toward the other open end through electrical heating elements, means being provided to periodically interrupt the flow of air.

10. An instrument as set forth in claim 8, wherein said applicator includes a suction fan disposed in said casing to draw air from one open end and blow it toward the other open end through electrical heating elements, and a scanner having disposed adjacent the other end and provided with an outlet nozzle, said scanner being caused to oscillate at a predetermined rate to cause said nozzle to discharge a high-velocity beam of air within a radiation sector which is swept by the nozzle.

11. An instrument as set forth in claim 7, wherein the high velocity stream which is generated therein is blown into a horizontal cylinder having a row of openings therein along a longitudinal axis with outlet ports being coupled to said openings; and a tubular air modulator rotating at a constant rate in said cylinder, said modulator having a series of arcuate slots therein at angularly displaced circumferential positions, each slot registering with a respective opening in the course of a full revolution of the modulator whereby beams of high-velocity are sequentially projected from the outlet ports.

12. In an instrument as set forth in claim 7, wherein the high velocity stream which is generated therein is blown into a vertical column having a row of openings therein along a longitudinal axis, each opening communicating with a hollow articulated arm cantilevered from the column and terminating in a downward outlet port, and an air modulator rotating at a constant rate in said column, said modulator having a series of arcuate slots therein at angularly displaced positions to register with a respective opening in the course of a full revolution of the modulator whereby beans of high-velocity air are sequentially projected from the outlet ports.

13. In an instrument as set forth in claim 7, wherein the high velocity stream which is generated therein is blown into a vertical column having a row of openings therein along a longitudinal axis, each opening communicating with a hollow articulated arm cantilevered from the column and terminating in a downward outlet port, and an air modulator rotating at a constant rate in said column, said modulator having a series of arcuate slots therein at angularly displaced positions to register with a respective opening in the course of a full revolution of the modulator whereby beams of high-velocity air are sequentially projected from the outlet ports.

14. An instrument as set forth in claim 13, including a heater to heat the stream of air to a temperature well above normal body temperature.

15. An instrument as set forth in claim 13, including means to reduce the temperature of the stream to a level well below normal body temperature.

* * * * *